United States Patent
Chen et al.

(10) Patent No.: US 10,857,108 B2
(45) Date of Patent: Dec. 8, 2020

(54) COMPOSITION FOR PREVENTING AND/OR TREATING CARDIOVASCULAR AND CEREBROVASCULAR DISEASES

(71) Applicants: Xiamen Kingdomway Group Company, Fujian (CN); Xiamen Kingdomway Biotech. Co., Ltd., Fujian (CN)

(72) Inventors: Fangfang Chen, Fujian (CN); Weicheng Liao, Fujian (CN); Huaying Liu, Fujian (CN); Suxia Xu, Fujian (CN)

(73) Assignees: Xiamen Kingdomway Group Company, Fujian (CN); Xiamen Kingdomway Biotech. Co., Ltd., Fujian (CN)

( * ) Notice: Subject to any disclaimer, the term of this patent is extended or adjusted under 35 U.S.C. 154(b) by 388 days.

(21) Appl. No.: 15/754,484

(22) PCT Filed: Aug. 19, 2016

(86) PCT No.: PCT/CN2016/095979
§ 371 (c)(1),
(2) Date: Aug. 6, 2018

(87) PCT Pub. No.: WO2017/032270
PCT Pub. Date: Mar. 2, 2017

(65) Prior Publication Data
US 2018/0353444 A1 Dec. 13, 2018

(30) Foreign Application Priority Data

Aug. 25, 2015 (CN) .......................... 2015 1 0522969

(51) Int. Cl.
| | | |
|---|---|---|
| *A61K 36/00* | (2006.01) | |
| *A61K 31/122* | (2006.01) | |
| *A61K 31/202* | (2006.01) | |
| *A61K 31/385* | (2006.01) | |
| *A61K 31/685* | (2006.01) | |
| *A23L 33/00* | (2016.01) | |
| *A61K 45/06* | (2006.01) | |
| *A61K 31/20* | (2006.01) | |
| *A61K 31/065* | (2006.01) | |
| *A61K 36/258* | (2006.01) | |
| *A61K 36/48* | (2006.01) | |
| *A61K 9/00* | (2006.01) | |
| *A61K 9/48* | (2006.01) | |
| *A23L 33/12* | (2016.01) | |

(52) U.S. Cl.
CPC .......... *A61K 31/122* (2013.01); *A23L 33/00* (2016.08); *A23L 33/12* (2016.08); *A61K 9/0053* (2013.01); *A61K 9/4875* (2013.01); *A61K 31/065* (2013.01); *A61K 31/20* (2013.01); *A61K 31/202* (2013.01); *A61K 31/385* (2013.01); *A61K 31/685* (2013.01); *A61K 36/258* (2013.01); *A61K 36/48* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,964,969 B2 | 11/2005 | McCleary |
| 8,337,931 B2 | 12/2012 | Bromley |
| 8,865,687 B2 | 10/2014 | Kiliaan et al. |

FOREIGN PATENT DOCUMENTS

| | | |
|---|---|---|
| CN | 1440240 A | 9/2003 |
| CN | 102131407 A | 7/2011 |
| CN | 102232553 A | 11/2011 |
| CN | 102754829 A | 10/2012 |
| CN | 103565801 A | 2/2014 |
| CN | 104366475 A | 2/2015 |
| CN | 105079009 A | 11/2015 |

OTHER PUBLICATIONS

International Search Report for Application No. PCT/CN2016/095979 dated Nov. 30, 2016, 4 pages.
English language abstract for CN 1440240 extracted from espacenet.com database on Mar. 10, 2018, 2 pages.
English language abstract for CN 102131407 extracted from espacenet.com database on Mar. 10, 2018, 1 page.
English language abstract and machine-assisted English translation for CN 102754829 extracted from espacenet.com database on Mar. 10, 2018, 22 pages.
English language abstract and machine-assisted English translation for CN 105079009 extracted from espacenet.com database on Mar. 10, 2018, 31 pages.
English language abstract and machine-assisted English translation for CN 102232553 extracted from espacenet.com database on Feb. 10, 2020, 4 pages.
English language abstract and machine-assisted English translation for CN 103565801 extracted from espacenet.com database on Feb. 10, 2020, 14 pages.
English language abstract and machine-assisted English translation for CN 104366475 extracted from espacenet.com database on Feb. 10, 2020, 10 pages.

*Primary Examiner* — Qiuwen Mi
(74) *Attorney, Agent, or Firm* — Howard & Howard Attorneys PLLC

(57) ABSTRACT

The present invention relates to a composition for preventing and/or treating cardiovascular and cerebrovascular diseases, a method for preparing the same, and use thereof, wherein the composition comprises at least two of docosahexaenoic acid or an ester thereof, coenzyme Q10, lipoic acid and phospholipid. The composition is used for preparing a dietary supplement or health food, preferably, for preparing a dietary supplement or health food for preventing and/or treating dyslipidemia or cardiovascular and cerebrovascular diseases.

26 Claims, No Drawings

COMPOSITION FOR PREVENTING AND/OR TREATING CARDIOVASCULAR AND CEREBROVASCULAR DISEASES

CROSS-REFERENCE TO RELATED APPLICATIONS

The present application is the National Stage of International Patent Application No. PCT/CN2016/095979, filed on Aug. 19, 2016, which claims priority to and all the benefits of Application No. 201510522969.X, filed on Aug. 25, 2015 in China, which are hereby expressly incorporated herein by reference in their entirety.

TECHNICAL FIELD

The present invention relates to the fields of medicine and health food, in particular, to a composition for preventing and/or treating cardiovascular and cerebrovascular diseases.

BACKGROUND ART

Diseases of heart blood vessels and of brain blood vessels are collectively called as cardiovascular and cerebrovascular disease, and generally refer to ischemic or hemorrhagic diseases in the heart, brain and body tissues caused by hyperlipidemia, blood viscosity, atherosclerosis and hypertension etc. The diseases are common diseases that seriously threaten the health of human beings, especially those over the age of 50. Even though the most advanced and perfect treatment at present is applied, over 50% of survivors of cardiovascular and cerebrovascular accidents still cannot fully take care of their own lives. The number of people who die of cardiovascular and cerebrovascular diseases in the world is up to 15 million each year, ranking the top of all causes of death.

At present, as to cardiovascular and cerebrovascular diseases, prevention is still put first, and the main means include control of risk factors and antithrombosis. The risk factors of cardiovascular and cerebrovascular diseases are divided into two categories, namely, the risk factors that can be managed, such as hypertension, dyslipidemia, diabetes, and smoking etc., and the other risk factors that are not manageable, such as age, gender and heredity. It has been proved that controlling blood pressure within a normal range, treating diabetes, giving up smoking and treating dyslipidemia can significantly reduce the occurrence of cardiovascular and cerebrovascular events.

It has been disclosed in the prior art a variety of substances which exhibit certain effects on the prevention and treatment of cardiovascular and cerebrovascular diseases, but it have never revealed which combinations show a synergistic effect.

CONTENTS OF THE DESCRIPTION

By doing experiments continuously, the inventors of the present invention have surprisingly discovered combinations of a series of components that have protective effects on heart and brain blood vessels. The combinations have produced unexpected synergistic effects in the prevention and/or treatment of cardiovascular and cerebrovascular diseases. The present invention has been completed based on the above discoveries.

According to the first aspect of the present invention, there is provided a composition comprising at least two, for example two, three or four selected from a group consisting of docosahexaenoic acid or an ester thereof, coenzyme Q10, lipoic acid and phospholipid.

In one embodiment of the invention, the composition comprises a combination selected from any one of i) to xi) below:

docosahexaenoic acid or an ester thereof and coenzyme Q10;
ii) docosahexaenoic acid or an ester thereof and lipoic acid;
iii) docosahexaenoic acid or an ester thereof and phospholipid;
iv) coenzyme Q10 and lipoic acid;
v) coenzyme Q10 and phospholipid;
vi) lipoic acid and phospholipid;
vii) docosahexaenoic acid or an ester thereof, coenzyme Q10 and lipoic acid;
viii) docosahexaenoic acid or an ester thereof, coenzyme Q10 and phospholipid;
ix) docosahexaenoic acid or an ester thereof, lipoic acid and phospholipid;
x) coenzyme Q10, lipoic acid and phospholipid; and
xi) docosahexaenoic acid or an ester thereof, coenzyme Q10, lipoic acid and phospholipid;
preferably, the composition comprises a combination of docosahexaenoic acid or an ester thereof and coenzyme Q10;
more preferably, the composition comprises a combination of docosahexaenoic acid or an ester thereof, coenzyme Q10, lipoic acid and phospholipid.

The composition according to any one of the items in the first aspect of the present invention, wherein each component with content calculated according to the weight percentage is one or more selected from the following:

0.5 to 80% (e.g., 5 to 60%) of docosahexaenoic acid or an ester thereof;
2) 0.5 to 60% (e.g., 5 to 55%) of coenzyme Q10;
3) 0.5 to 60% (e.g., 5 to 50%) of lipoic acid; and
4) 0.1 to 60% (e.g., 2 to 35%) of phospholipid.

In one embodiment, the composition according to any one of the items in the invention, wherein a component, if presents, is one or more selected from the following:

3 to 50 parts by weight of the docosahexaenoic acid or an ester thereof (for example, 3 parts, 4 parts, 5 parts, 9 parts, 10 parts, 19 parts, 20 parts, 38 parts, 39 parts or 50 parts; further for example, 5-39 parts, 18-23 parts or 9-19 parts);
b) 3 to 60 parts by weight of the coenzyme Q10 (for example, 3 parts, 4 parts, 5 parts, 9 parts, 10 parts, 19 parts, 20 parts, 49 parts, 50 parts or 60 parts; further for example, 4-50 parts, 5-20 parts, 9-19 parts or 8-13 parts);
c) 3 to 50 parts by weight of the lipoic acid (for example, 3 parts, 4 parts, 5 parts, 9 parts, 10 parts, 19 parts, 20 parts, 39 parts, 40 parts or 50 parts; further for example, 4-40 parts, 9-20 parts, 20-30 parts, 30-40 parts or 38-43 parts); and
d) 1 to 40 parts by weight of the phospholipid (for example, 1 part, 2 parts, 3 parts, 4 parts, 5 parts, 9 parts, 10 parts, 29 parts, 30 parts or 40 parts; further for example, 5-10 parts, 10-20 parts, 2-30 parts, 30-40 parts or 3-8 parts).

In one embodiment, the composition comprises a combination selected from any one of i) to xi) below:

docosahexaenoic acid or an ester thereof and coenzyme Q10, the parts by weight thereof being 18-23 and 8-13, respectively;
ii) docosahexaenoic acid or an ester thereof and lipoic acid, the parts by weight thereof being 18-23 and 38-43, respectively;

iii) docosahexaenoic acid or an ester thereof and phospholipid, the parts by weight thereof being 18-23 and 3-8, respectively;

iv) coenzyme Q10 and lipoic acid, the parts by weight thereof being 8-13 and 38-43, respectively;

v) coenzyme Q10 and phospholipid, the parts by weight thereof being 8-13 and 3-8, respectively;

vi) lipoic acid and phospholipid, the parts by weight thereof being 38-43 and 3-8, respectively;

vii) docosahexaenoic acid or an ester thereof, coenzyme Q10 and lipoic acid, the parts by weight thereof being 18-23, 8-13 and 38-43, respectively;

viii) docosahexaenoic acid or an ester thereof, coenzyme Q10 and phospholipid, the parts by weight thereof being 18-23, 8-13 and 3-8, respectively;

ix) docosahexaenoic acid or an ester thereof, lipoic acid and phospholipid, the parts by weight thereof being 18-23, 38-43 and 3-8, respectively;

x) coenzyme Q10, lipoic acid and phospholipid, the parts by weight thereof being 8-13, 38-43 and 3-8, respectively; and xi) docosahexaenoic acid or an ester thereof, coenzyme Q10, lipoic acid and phospholipid, the parts by weight thereof being 3-43, 3-53, 3-43 and 1-33, respectively; preferably, the parts by weight thereof being 18-23, 8-13, 38-43 and 3-8, respectively.

The composition according to any one of the items in the first aspect of the present invention, which comprises 0.5-80% (as calculated as a percentage by weight) of docosahexaenoic acid or an ester thereof, for example 5-80%, for example 5-60%, for example 5-57%, for example 5-40%, for example 5-30%, for example 5-25%, for example 5-10%, for example 10-57%, for example 10-40%, for example 10-30%, for example 10-25%, for example 10-20%, for example 20-57%, for example 20-40%, for example 20-30%, for example 20-25%, for example 30-57%, for example 30-40%, for example 40-57%.

In the embodiments of the invention, the docosahexaenoic acid or an ester thereof is a microbial fermentation extract; preferably, the microorganism is selected from a group consisting of *Ulkenia* sp., *Dinoflagellate, Schizochytrium* sp., *Crypthecodinium* sp., diatoms and *chlorella.*

In the embodiments of the invention, the ester of docosahexaenoic acid is one or more selected from a group consisting of methyl docosahexaenoate, ethyl docosahexaenoate, glyceryl docosahexaenoate, isopropyl docosahexaenoate, and docosahexaenoic acid-phospholipid.

The composition according to any one of the items in the first aspect of the present invention, which comprises 0.5-60% (as calculated as a percentage by weight) of coenzyme Q10, for example 5-60%, 5-55%, for example 5-40%, for example 5-30%, for example 5-20%, for example 5-10%, for example 10-55%, for example 10-40%, for example 10-30%, for example 10-20%, for example 20-55%, for example 20-40%, for example 20-30%, for example 30-55%, for example 30-40%, for example 40-55%.

In the embodiments of the invention, the coenzyme Q10 is a microbial fermentation extract; preferably, the microorganism is selected from a group consisting of *Rhodospirillum rubrum, Rhodopseudomonas palustris, Rhodobacter sphaeroides, Rhodovulum sulfidophilus* and *Rhodopseudomonas capsulate.*

In the embodiments of the invention, the coenzyme Q10 is selected from one or two of oxidized coenzyme Q10 and reduced coenzyme Q10.

The composition according to any one of the items in the first aspect of the present invention, which comprises 0.5-60% (as calculated as a percentage by weight) of lipoic acid, for example 5-60%, for example 5-50%, for example 5-40%, for example 5-30%, for example 5-20%, for example 5-10%, for example 10-50%, for example 10-40%, for example 10-30%, for example 10-20%, for example 20-50%, for example 20-40%, for example 20-30%, for example 30-50%, for example 30-40%, for example 40-50%.

In the embodiments of the invention, the lipoic acid is selected from one or two of oxidized lipoic acids and reduced lipoic acids; preferably, the reduced lipoic acid is dihydrolipoic acid.

The composition according to any one of the items in the first aspect of the present invention, which comprises 0.1-60% (as calculated as a percentage by weight) of phospholipid, for example 2-50%, for example 2-35%, for example 2-30%, for example 2-15%, for example 2-10%, for example 10-35%, for example 10-30%, for example 10-20%, for example 20-35%, for example 20-30%, for example 30-35%, for example 5%, for example 20%.

In the embodiments of the invention, the phospholipid is one or more selected from a group consisting of hydroxylated phospholipid, phosphatidylcholine, phosphatidylethanolamine, phosphatidylserine, phosphatidylglycerol, diphosphatidylglycerol, phosphatidylinositol, sphingomyelin and the like; preferably, the phospholipid is selected from hydroxylated lecithin and phosphatidylserine.

In one embodiment of the invention, the phospholipid is a natural soybean extract.

The composition according to any one of the items in the first aspect of the present invention, which further comprises one or more (for example, two, three, four, or five) selected from a group consisting of proanthocyanidins, soy isoflavone, lutein, *Panax* notoginsenosides and beta-glucan.

The composition according to any one of the items in the first aspect of the present invention, wherein the amount of each component calculated according to the weight percentage is selected from one or more:

0.1-15% (e.g., 0.1-11%) of proanthocyanidins;
(2) 0.1-8% (e.g., 0.1-5.5%) of soy isoflavone;
(3) 0.1-10% (e.g., 0.5-10%) of lutein;
(4) 0.1-8% (e.g., 0.1-6%) of *Panax* notoginsenosides; and
(5) 0.1-8% (e.g., 0.1-6%) β-glucan.

In one embodiment, the composition according to any one of the items in the invention further comprises one or more of the following: proanthocyanidins, soy isoflavone, lutein, *Panax* notoginsenosides and β-glucan, for example, the composition further comprises a combination selected from any one of the following 1) to 9):

proanthocyanidins, soy isoflavon and lutein;
2) proanthocyanidins, soy isoflavone and *Panax* notoginsenosides;
3) proanthocyanidins, soy isoflavone and β-glucan;
4) proanthocyanidins, lutein and *Panax* notoginsenosides;
5) proanthocyanidins, lutein and β-glucan;
6) proanthocyanidins, *Panax* notoginsenosides and β-glucan;
7) soy isoflavone, lutein and *Panax* notoginsenosides;
8) soy isoflavone, lutein and β-glucan; and
9) soy isoflavone, *Panax* notoginsenosides and β-glucan;

preferably, the composition further comprises a combination selected from any one of the following 1), 7) and 10)-14):

proanthocyanidins, soy isoflavone and lutein;
7) soy isoflavone, lutein and *Panax* notoginsenosides;
10) lutein, *Panax* notoginsenosides and β-glucan;
11) proanthocyanidins, soy isoflavone, lutein and *Panax* notoginsenosides;

12) proanthocyanidins, soy isoflavone, lutein and β-glucan;

13) proanthocyanidins, lutein, Panax notoginsenosides and β-glucan; and 14) soy isoflavone, lutein, Panax notoginsenosides and β-glucan;

more preferably, the composition further comprises a combination selected from any one of the following 11), 14) and 15):

11) proanthocyanidins, soy isoflavone, lutein and Panax notoginsenosides;

14) soy isoflavone, lutein, Panax notoginsenosides and β-glucan; and 15) proanthocyanidins, soy isoflavone, lutein, Panax notoginsenosides and β-glucan;

further more preferably, the composition further comprises the combination described in following 15):

15) proanthocyanidins, soy isoflavone, lutein, Panax notoginsenosides and β-glucan.

In one embodiment, the composition according to any one of items in the invention, wherein a component, if presents, is one or more selected from the following:

e) 0.5 to 15 parts by weight of the proanthocyanidins (for example 0.5 part, 1 part, 2 parts, 3 parts, 4 parts, 8 parts, 9 parts or 10 parts; for example 0.5-10 parts, 1-8 parts, 2-4 parts, or 1.8-2.3 parts);

f) 0.1 to 6 parts by weight of the soy isoflavone (for example, 0.1 part, 0.2 part, 0.3 part, 0.4 part, 0.5 part, 1.3 parts, 1.6 parts, 3.2 parts or 4 parts; further for example, 0.1-4 parts, 0.5-3.2 parts, 1.3-1.6 parts or 0.3-0.5 part);

g) 0.1 to 12 parts by weight of the lutein (for example, 0.3 part, 0.4 part, 0.7 part, 0.8 part, 1.5 parts, 1.6 parts, 1.8 parts, 3.3 parts, 3.6 parts, 7.3 parts, 8.1 parts or 9 parts; further for example, 0.3-9 parts, 1-8 parts, 3-7 parts or 1.3-1.8 parts);

h) 0.1-6 parts by weight of the Panax notoginsenosides (for example, 0.1 part, 0.2 part, 0.3 part, 0.4 part, 0.5 part, 0.6 part, 0.8 part, 1.3 parts, 1.6 parts, 3.2 parts or 4 parts; further for example 0.2-4 parts, 0.5-3 parts, 1-2 parts or 0.3-0.5 part); and 0.1 to 6 parts by weight of the β-glucan (for example, 0.1 part, 0.2 part, 0.3 part, 0.4 part, 0.5 part, 1.2 parts, 1.6 parts, 3.0 parts, 3.6 parts or 4 parts; further for example, 0.1-4 parts, 0.3-3 parts, 0.5-1.6 parts or 0.3-0.5 part).

In one embodiment, the composition according to any one of items in the invention further comprises one or more of the following: proanthocyanidins, soy isoflavone, lutein, Panax notoginsenosides and β-glucan, for example, the composition further comprises a combination selected from any one of the following 1) to 9):

proanthocyanidins, soy isoflavon and lutein, the parts by weight thereof being 1.8-2.3, 0.3-0.5 and 1.3-1.8, respectively;

2) proanthocyanidins, soy isoflavone and Panax notoginsenosides, the parts by weight thereof being 1.8-2.3, 0.3-0.5 and 0.3-0.5, respectively;

3) proanthocyanidins, soy isoflavone and β-glucan, the parts by weight thereof being 1.8-2.3, 0.3-0.5 and 0.3-0.5, respectively;

4) proanthocyanidins, lutein and Panax notoginsenosides, the parts by weight thereof being 1.8-2.3, 1.3-1.8 and 0.3-0.5, respectively;

5) proanthocyanidins, lutein and β-glucan, the parts by weight thereof being 1.8-2.3, 0.3-0.5 and 0.3-0.5, respectively;

6) proanthocyanidins, Panax notoginsenosides and β-glucan, the parts by weight thereof being 1.8-2.3, 1.3-1.8 and 0.3-0.5, respectively;

7) soy isoflavone, lutein and Panax notoginsenosides, the parts by weight thereof being 0.3-0.5, 1.3-1.8 and 0.3-0.5, respectively;

8) soy isoflavone, lutein and β-glucan, the parts by weight thereof being 0.3-0.5, 1.3-1.8 and 0.3-0.5, respectively; and 9) soy isoflavone, Panax notoginsenosides and β-glucan, the parts by weight thereof being 0.3-0.5, 0.3-0.5 and 0.3-0.5, respectively;

preferably, the composition further comprises a combination selected from any one of the following 1), 7) and 10)-14):

proanthocyanidins, soy isoflavone and lutein, the parts by weight thereof being 1.8-2.3, 0.3-0.5 and 1.3-1.8, respectively;

7) soy isoflavone, lutein and Panax notoginsenosides, the parts by weight thereof being 0.3-0.5, 1.3-1.8 and 0.3-0.5, respectively;

10) lutein, Panax notoginsenosides and β-glucan, the parts by weight thereof being 1.3-1.8, 0.3-0.5 and 0.3-0.5, respectively;

11) proanthocyanidins, soy isoflavone, lutein and Panax notoginsenosides, the parts by weight thereof being 1.8-2.3, 0.3-0.5, 1.3-1.8 and 0.3-0.5, respectively;

12) proanthocyanidins, soy isoflavone, lutein and β-glucan, the parts by weight thereof being 1.8-2.3, 0.3-0.5, 1.3-1.8 and 0.3-0.5, respectively;

13) proanthocyanidins, lutein, Panax notoginsenosides and β-glucan, the parts by weight thereof being 1.8-2.3, 1.3-1.8, 0.3-0.5 and 0.3-0.5, respectively; and 14) soy isoflavone, lutein, Panax notoginsenosides and β-glucan, the parts by weight thereof being 0.3-0.5, 1.3-1.8, 0.3-0.5 and 0.3-0.5, respectively;

more preferably, the composition further comprises a combination selected from any one of the following 11), 14) and 15):

11) proanthocyanidins, soy isoflavone, lutein and Panax notoginsenosides, the parts by weight thereof being 1.8-2.3, 0.3-0.5, 1.3-1.8 and 0.3-0.5, respectively;

14) soy isoflavone, lutein, Panax notoginsenosides and β-glucan, the parts by weight thereof being 0.3-0.5, 1.3-1.8, 0.3-0.5 and 0.3-0.5, respectively; and 15) proanthocyanidins, soy isoflavone, lutein, Panax notoginsenosides and β-glucan, the parts by weight thereof being 0.5-10, 0.1-4, 0.3-9, 0.2-4 and 0.1-4, respectively; preferably, the parts by weight thereof being 1.8-2.3, 0.3-0.5, 1.3-1.8, 0.3-0.5 and 0.3-0.5, respectively;

further more preferably, the composition further comprises the combination described in following 15):

15) proanthocyanidins, soy isoflavone, lutein, Panax notoginsenosides and β-glucan, the parts by weight thereof being 0.5-10, 0.1-4, 0.3-9, 0.2-4 and 0.1-4, respectively, preferably, the parts by weight thereof being 1.8-2.3, 0.3-0.5, 1.3-1.8, 0.3-0.5 and 0.3-0.5, respectively.

In one embodiment of the invention, the composition further comprises proanthocyanidins, soy isoflavone, lutein and Panax notoginsenosides, or soy isoflavone, lutein, Panax notoginsenosides and β-glucan, or proanthocyanidins, soy isoflavone, lutein, Panax notoginsenosides and β-glucan, and in this case, the mass ratio of each of the components is (1-400):(2-250):(1-200):(5-20):(2-5):1:(2-5):(0.1-5):(0.1-5).

In one embodiment of the invention, the composition comprises docosahexaenoic acid or an ester thereof, coenzyme Q10, lipoic acid, phospholipid, proanthocyanidins, soy isoflavone, lutein, Panax notoginsenoside and β-glucan, and in this case, the mass ratio of each of the components is (1-400):(2-250):(1-200):(5-20):(2-5):1:(2-5):(0.1-5):(0.1-5).

The composition according to any one of the items in the first aspect of the present invention comprises 0.1-15% by weight of proanthocyanidins, for example 0.1-11% by weight, for example 0.1-1% by weight, for example 1-11% by weight.

In one embodiment of the invention, the proanthocyanidins is from a grape seed extract.

The composition according to any one of the items in the first aspect of the present invention comprises 0.1-8% by weight of soy isoflavone, for example, 0.1-5.5% by weight.

In one embodiment of the invention, the soy isoflavone is from a soybean germ extract.

The composition according to any one of the items in the first aspect of the present invention comprises 0.1-10% by weight of lutein, for example, 0.1-1% by weight, for example 1-10% by weight, for example 0.5-10% by weight, for example 0.5-5% by weight.

In one embodiment of the invention, the lutein is from a marigold extract.

The composition according to any one of the items in the first aspect of the present invention comprises 0.1-8% by weight of *Panax* notoginsenosides, for example, 0.1-6% by weight, for example 0.1-1% by weight, for example 0.1-3% by weight, for example 1-6% by weight.

In one embodiment of the invention, the *Panax* notoginsenosides are from a *Panax notoginseng* extract.

The composition according to any one of the items in the first aspect of the present invention comprises 0.1-8% by weight of β-glucan, for example, 0.1-6% by weight, for example 0.1-1% by weight, for example 0.1-3% by weight, for example 1-6% by weight.

In one embodiment of the invention, the β-glucan is from an oat extract.

In one embodiment, the composition according to any one of the items in the present invention further comprises a carrier oil, preferably, if present, the carrier oil is present in 0.1-85 parts by weight.

In one embodiment, the composition according to any one of the items in the present invention is balanced with a carrier oil.

The composition according to any one of the items in the first aspect of the present invention is balanced with a carrier oil.

In embodiments of the invention, the carrier oil is one or more selected from a group consisting of natural vegetable fats, natural animal fats and synthetic fats, which are selected from one or more of a group consisting of soybean oil, rapeseed oil, olive oil, sesame oil, corn oil, palm oil, sunflower oil, mustard oil, rice bran oil, coconut oil, linseed oil, evening primrose oil, garlic oil, jojoba oil, lard, tallow, fish oil, butter and medium chain triglycerides; preferably, the medium-chain triglyceride is selected from one or two of saturated caprylic triglyceride and saturated capric triglyceride.

In one embodiment, in the composition according to any one of the items in the present invention, the medium chain triglyceride is one or more selected from a group consisting of saturated caprylic triglyceride and saturated capric triglyceride and caprylic/capric triglyceride; preferably, the carrier oil at least comprises caprylic/capric triglyceride.

The composition according to any one of the items in the first aspect of the present invention is in a dosage form such as oils or suspensions, or is soft capsules, hard capsules, microcapsules, tablets, powders, pills, emulsions or suspensions, which are formed together with adjuvants.

The second aspect of the present invention provides a method for preparing a composition according to any one of items in the first aspect of the present invention, which comprises the following steps:

Weighing each component and mixing to obtain the composition; preferably, a filtering step is further included following the mixing step; more preferably, a step of removing bubbles is further included following the mixing step.

In embodiments of the present invention, the step of being mixed can be performed by using at least one of conventional stirring, shear emulsification and high-pressure homogenization; preferably, the step of being mixed is performed at 30° C. to 80° C., preferably 50° C. to 70° C., such as 60° C.; preferably, the step of being mixed is performed in an environment of vacuum or inert gas.

The third aspect of the present invention provides a use of the composition according to any one of the items in the first aspect of the present invention in the manufacture of a dietary supplement or health food, preferably in the manufacture of a dietary supplement or health food for preventing and/or treating dyslipidemia or cardiovascular and cerebrovascular diseases.

The fourth aspect of the present invention provides a use of the composition according to any one of the items in the first aspect of the present invention in the manufacture of a medicament for preventing and/or treating dyslipidemia or cardiovascular and cerebrovascular diseases.

The fifth aspect of the present invention provides a composition according to any one of the items in the first aspect of the present invention, for use in the prevention and/or treatment of dyslipidemia or cardiovascular and cerebrovascular diseases.

The sixth aspect of the present invention provides a method for preventing and/or treating dyslipidemia or cardiovascular and cerebrovascular diseases in an individual in need thereof, comprising a step of administering to the individual a therapeutically effective amount of the composition according to any one of the items in the present invention.

In the embodiments of the invention, the dyslipidemia includes hyperlipidemia (e.g., hypercholesterolemia and/or hypertriglyceridemia), or one or more selected from elevated total cholesterol in the blood, elevated low-density lipoprotein cholesterol in the blood, elevated triglycerides in the blood, and reduced high-density lipoprotein cholesterol in the blood.

In the embodiments of the invention, the cardiovascular and cerebrovascular disease is selected from arteriosclerosis, hypertension, hyperlipidemia, cerebral infarction, cerebral hemorrhage, coronary heart disease, angina pectoris, myocardial ischemia, myocardial infarction, heart failure and arrhythmia.

Various aspects and features of the present invention are further described below.

The various terms and phrases used in the present invention have their ordinary meanings well known to those skilled in the art, and even if so, the present invention still intends to further explain these terms and phrases again in a more complete sense. If the terms and phrases mentioned are not consistent to the ordinary meanings well known in the art, the meanings expressed in the present invention shall prevail.

As used herein, the term "docosahexaenoic acid" is DHA.

The "extract" in the present invention is either commercially available or prepared by extraction methods well known in the art, and the source of the extract does not constitute a limitation on each of the components of the composition of the present invention.

As used herein, the term "phospholipid" includes phosphatidylcholine, phosphatidylethanolamine, phosphatidylserine, phosphatidylglycerol, diphosphatidylglycerol, phosphatidylinositol and sphingomyelin etc.

As used herein, the term "coenzyme Q10" includes oxidized and reduced forms, and is a fat-soluble antioxidant.

As used herein, the term "lipoic acid" is a sulfur-containing $C_8$-fatty acid and an enzyme present in mitochondria, and can be converted into reduced dihydrolipoic acid in mammalian cells.

As used herein, the term "grape seed extract" is a potent active nutrient extracted from natural grape seeds and is rich in proanthocyanidins and polyphenols. The proanthocyanidins, referred to as OPC, are internationally recognized as the most effective natural antioxidants to remove free radicals in the human body.

As used herein, the term "marigold extract" is enriched in lutein and zeaxanthin. The said lutein is also called as carotenoid, carotol, plant lutein, nuclear lutein, patuletin and plant xanthophyll.

As used herein, the term "soy isoflavone" is a type of secondary metabolite formed during the growth of soybeans.

As used herein, the term "*Panax notoginseng* extract" is rich in *Panax* notoginsenosides.

As used herein, the term "oat extract" is rich in β-glucan.

As used herein, the term "dietary supplement" is also referred to as nutritional supplement, nutritional supplementation product, nutrient, dietary supplement and the like, and is used as an aid to the diet for supplementing amino acids required by the human body, and trace elements, vitamins, minerals, etc., to achieve the purpose of improving the health of body and reducing the risk of diseases.

The composition of the present invention may be administered in any known modes such as oral, intramuscular, subcutaneous administration and the like, and administration dosage forms thereof are such as tablets (for example, buccal tablets, chewable tablets), capsules (for example, soft capsules, hard capsules, microcapsules), oils, powders, pills, emulsions and suspensions, elixirs, transdermal agents, microencapsulants, implants, syrups and the like. The composition can be present in general formulations, sustained release formulations, controlled release formulations and various particle delivery systems. The preparation of various dosage forms can be made by reference to the teachings of textbooks in the art. To formulate unit dosage forms into tablets, a wide variety of biodegradable or biocompatible carriers well known in the art may be employed. The pharmaceutically acceptable carriers comprised in the compositions of the present invention include, but are not limited to, ion exchangers, alumina, aluminum stearate, lecithin, serum proteins such as human serum proteins, buffer substances such as phosphates, glycerol, sorbic acid, potassium sorbate, a mixture of a part of glycerides of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinylpyrrolidone, cellulosic materials, polyethylene glycol, carboxymethylcellulose sodium, polyacrylates, beeswax, wool vinegar and the like. The carrier may be present in the pharmaceutical composition in an amount of from 1% by weight to 98% by weight and usually at about 80% by weight. For convenience, local anesthetics, preservatives, buffers and the like may be dissolved directly into the carrier.

The administration dose of the composition of the present invention depends on many factors, for example, the nature and severity of a disease to be prevented or treated, the gender, age, weight, sensitivity and individual response of a patient or animal, particularly employed compound, administration route, administration frequency, and desired therapeutic effect etc. The above dose may be administered in a single dosage form or by dividing into several (e.g., two, three or four etc.) dosage forms. The single maximum dose will generally not exceed 30 mg/Kg body weight, for example 0.001-30 mg/Kg, preferably 0.01-5 mg/Kg, and a better dose range is of from 0.5 to 2 mg/Kg body weight. However, in some cases it is also possible to use a single dose of above 30 mg/Kg body weight or of below 0.001 mg/Kg.

Advantageous Effects of the Invention

The present invention provides combinations of a series of components having cardiovascular and cardiovascular protective effects, which combinations have achieved unexpected synergistic effects in the prevention and/or treatment of cardiovascular and cerebrovascular diseases. In an animal model of lipid metabolism disorder, the composition of the present invention can effectively reduce the levels of total cholesterol (TC) and triglyceride (TG) and can significantly increase the level of high-density lipoprotein cholesterol (HDL-C) in serum of rats, exhibiting obvious synergies as compared with the application of a single component.

Specific Mode for Carrying Out the Invention

The embodiments of the present invention will be described in detail below with reference to examples. However, those skilled in the art will understand that the following examples are only for illustrating the present invention but should not be construed as limiting the scope of the present invention. In the examples, the specific conditions which are not specified are performed according to the usual conditions or conditions proposed by the manufacturer, and the used reagents or instruments whose manufacturers are not specified all are conventional products that are commercially available.

The materials used in Examples 1-37 are commercially available and are food-grade or pharmaceutical grade. The specifications of main raw materials are shown in Table 1, and the formulae of the compositions are shown in Table 2.

TABLE 1

Specifications of main raw materials

| Name of raw material | Specification |
| --- | --- |
| DHA algal oil | Amount of docosahexaenoic acid being of 55% |
| Oxidized coenzyme Q10 | Amount of oxidized coenzyme Q10 being of 98% |
| Reduced coenzyme Q10 | Amount of reduced coenzyme Q10 being of 98% |
| Oxidized lipoic acid | Amount of oxidized lipoic acid being of 99% |
| Dihydrolipoic acid | Amount of dihydrolipoic acid being of 99% |
| Soybean phospholipid | Amount of total phosphorus being of 60% |
| Phosphatidylserine | Amount of phosphatidylserine being of 98% |
| Modified phospholipid | Amount of hydroxylated lecithin being of 60% |
| Grape seed extract | Amount of proanthocyanidins being of 99% |
| Soybean germ extract | Amount of soy isoflavone being of 80% |
| Marigold extract | Amount of lutein being of 90% |
| *Panax notoginseng* extract | Amount of *Panax* notoginsenosides being of 80% |
| Oat extract | Amount of β-glucan being of 75% |

TABLE 2 formulae of examples 1-37

| Ex. | DHA algae oil (g) | oxidized coenzyme Q10 (g) | reduced coenzyme Q10 (g) | oxidized lipoic acid (g) | Dihydrolipoic acid (g) | Soybean phospholipid (g) | Phosphatidylserine (g) | Modified phospholipid (g) | Grape seed extract (g) | Soybean germ extract (g) | Marigold extract (g) | *Panax notoginseng* extract (g) | Oat extract (g) | Soybean oil (g) | Garlic oil (g) | caprylic/capric triglyceride (g) |
|---|---|---|---|---|---|---|---|---|---|---|---|---|---|---|---|---|
| 1 | 36 | / | / | / | / | / | / | / | / | / | / | / | / | 64 | / | / |
| 2 | / | / | 10 | / | / | / | / | / | / | / | / | / | / | 90 | / | / |
| 3 | / | / | / | / | 40 | / | / | / | / | / | / | / | / | 60 | / | / |
| 4 | / | / | / | / | / | 8 | / | / | / | / | / | / | / | 92 | / | / |
| 5 | / | / | / | / | / | / | / | / | / | / | / | / | / | 98 | / | / |
| 6 | / | / | / | / | / | / | / | / | / | / | / | / | / | 99.4 | / | / |
| 7 | / | / | / | / | / | / | / | / | 2 | / | / | / | / | 98 | / | / |
| 8 | 36 | / | 10 | / | 40 | 8 | / | / | / | 0.6 | 2 | 0.6 | 0.7 | 99.4 | / | / |
| 9 | / | / | / | / | / | / | / | / | / | / | / | / | / | 99.3 | / | / |
| 10 | 36 | / | 10 | / | 40 | 8 | / | / | 2 | 0.6 | / | / | / | 54 | / | / |
| 11 | 36 | / | 10 | / | 40 | 8 | / | / | / | / | / | / | / | 24 | / | / |
| 12 | 36 | / | 10 | / | 40 | 8 | / | / | / | / | / | / | / | 56 | / | / |
| 13 | / | / | / | / | / | 8 | / | / | / | / | / | / | / | 50 | / | / |
| 14 | 36 | / | 10 | / | 40 | 8 | / | / | / | / | / | / | / | 82 | / | / |
| 15 | 36 | / | 10 | / | 40 | 8 | / | / | / | / | / | / | / | 14 | / | / |
| 16 | / | / | / | / | / | / | / | / | / | / | / | / | / | 46 | / | / |
| 17 | 36 | / | 10 | / | 40 | 8 | / | / | / | 0.6 | / | / | / | 42 | / | / |
| 18 | 36 | / | 10 | / | 40 | 8 | / | / | 2 | / | 2 | / | / | 6 | / | / |
| 19 | 36 | / | 10 | / | 40 | 8 | / | / | 2 | / | / | / | / | 4 | / | / |
| 20 | 36 | / | 10 | / | 40 | 8 | / | / | 2 | 0.6 | 2 | / | / | 3.4 | / | / |
| 21 | 36 | / | 10 | / | 40 | 8 | / | / | 2 | 0.6 | 2 | 0.6 | / | 1.4 | / | / |
| 22 | 36 | / | 10 | / | 40 | 8 | / | / | 2 | 0.6 | 2 | 0.6 | 0.1 | 0.8 | / | / |
| 23 | 36 | / | 10 | / | 40 | 8 | / | / | 2 | 0.6 | 2 | 0.6 | 0.7 | 0.1 | / | / |
| 24 | 36 | / | 10 | / | 40 | 8 | / | / | 2 | 0.6 | 2 | 0.6 | 0.7 | 2.1 | / | / |
| 25 | 36 | / | 10 | / | 40 | 8 | / | / | 2 | 0.6 | 2 | 0.6 | 0.7 | 2.7 | / | / |
| 26 | 36 | / | 10 | / | 40 | 8 | / | / | / | 0.6 | / | / | 0.7 | 4.7 | / | / |
| 27 | 36 | / | 10 | / | 40 | 8 | / | / | / | 0.6 | 2 | 0.6 | / | 3.4 | / | / |
| 28 | 36 | / | 10 | / | 40 | / | 5 | 8 | 2 | 0.6 | 2 | 0.6 | 0.7 | 2.8 | / | / |
| 29 | 36 | / | 10 | / | 40 | / | / | 8 | 2 | 0.6 | 2 | 0.6 | 0.7 | 3.4 | / | / |
| 30 | 36 | / | 10 | / | 40 | / | 5 | / | 2 | 0.6 | 2 | 0.6 | 0.7 | 3.1 | / | / |
| 31 | 36 | 10 | / | 40 | / | / | / | / | 2 | 0.6 | 2 | 0.6 | 0.7 | / | / | / |
| 32 | 36 | 10 | / | 40 | / | / | / | / | 2 | 0.6 | 2 | 0.6 | 0.7 | / | / | / |
| 33 | 36 | / | 10 | / | 10 | / | 10 | / | 4 | 2.5 | 4.5 | 6.25 | 7 | / | / | / |
| 34 | 18 | / | 20 | / | 20 | / | 2 | / | 0.5 | 0.125 | 0.55 | 0.25 | 0.28 | / | 0.1 | 0.1 |
| 35 | 70 | 5 | / | 30 | / | / | 4 | / | 1 | 0.25 | 1 | 1.25 | 0.14 | / | 3.1 | 1.295 |
| 36 | 9 | 50 | / | / | / | / | / | / | / | / | / | / | / | / | 17.75 | 3.36 |
| 37 | 9 | / | 10 | 5 | / | / | 30 | / | 10 | 6.25 | 10 | 2.5 | 2.85 | / | 14.4 | / |

Preparing Method:

The ingredients in a ratio shown in Table 2 were weighed and mixed. The mixture was placed in a sealed container. The sealed container was vacuumized and supplemented with nitrogen for three times, and heated to 60° C. The ingredients in the container were agitated to be dissolved or evenly mixed, and bubbles were removal finally by ultrasonic wave to obtain a corresponding product.

Example 38 Test on Function to Reduce Blood Lipid Levels

Principle

Animal models of lipid metabolism disorder could be established by feeding animals with a feed having a high concentration of cholesterol and fats, and then the animals were administered with a test sample. The influences of the test sample on hyperlipidemia could be detected, and the influences of the test sample on the absorption of lipids, formation of lipoproteins, and degradation or excretion of lipids could be determined.

2. Instruments and Reagents

Anatomical instruments, spectrophotometer, automatic biochemical analyzer, and kits for determining cholesterol, bile salts, serum total cholesterol (TC), triglyceride (TG) and/or high-density lipoprotein (HDL-C).

3. Animal Selection and Feeds

Healthy male SD rats weighing 150-200 g were selected, and each group had 10 rats.

High-fat feed: 78.8% basal feed, 1% cholesterol, 10% egg yolk powder, 10% lard, and 0.2% bile salt.

Standard feed: basal feed

4. Methods

The test included 39 groups, wherein the first group was a control group of high-fat diet (i.e., given the high-fat feed), the second group was a group of standard diet (i.e., given with standard feed), and the remaining groups were given high-fat diet daily while administrated with a test sample prepared in Examples 1 to 37 by oral gavage, respectively, 2 ml each time, 3 times a day, for a test period of 30 days.

5. Experimental Steps

Under the experimental conditions, rats were fed with the basal feed and observed for 10 days. Blood was taken from the tails for determining the levels of total cholesterol (TC), triglyceride (TG), and high density lipoprotein cholesterol (HDL-C) in serum. According to the levels of TC, the rats were randomly divided into 39 groups and reared according to the method described in item 4 above. The rats were weighed regularly, and fasted for 16 hours at the end of the experiment. The levels of TC, TG and HDL-C in serum were determined. The results were shown in Tables 3-5.

TABLE 3

Serum total cholesterol (TC) test results

| Group No. | Diet | Mean total cholesterol (mg/dL) ± standard error | Decrease (%) | Student's t test P< | VS |
|---|---|---|---|---|---|
| 1 | Control (high-fat diet) | 546.8 ± 23.1 | — | — | — |
| 2 | Standard diet | 218.7 ± 17.3 | 60 | 0.001 | Control group |
| 3 | Test sample in example 1 | 426.5 ± 23.5 | 22 | 0.05 | Control group |
| 4 | Test sample in example 2 | 437.4 ± 25.8 | 20 | 0.05 | Control group |
| 5 | Test sample in example 3 | 492.1 ± 24.5 | 10 | NS | Control group |
| 6 | Test sample in example 4 | 508.5 ± 29.2 | 7 | NS | Control group |
| 7 | Test sample in example 5 | 535.8 ± 25.4 | 2 | NS | Control group |
| 8 | Test sample in example 6 | 541.3 ± 21.7 | 1 | NS | Control group |
| 9 | Test sample in example 7 | 535.9 ± 25.4 | 2 | NS | Control group |
| 10 | Test sample in example 8 | 541.3 ± 29.1 | 1 | NS | Control group |
| 11 | Test sample in example 9 | 535.9 ± 28.9 | 2 | NS | Control group |
| 12 | Test sample in example 10 | 300.7 ± 26.6 | 45 | 0.001 | Control group |
| 13 | Test sample in example 11 | 355.7 ± 25.4 | 35 | 0.01 | Control group |
| 14 | Test sample in example 12 | 377.3 ± 26.5 | 31 | 0.01 | Control group |
| 15 | Test sample in example 13 | 366.4 ± 20.1 | 33 | 0.01 | Control group |
| 16 | Test sample in example 14 | 393.7 ± 18.6 | 28 | 0.01 | Control group |
| 17 | Test sample in example 15 | 240.6 ± 24.6 | 56 | 0.001 | Control group |
| 18 | Test sample in example 16 | 267.9 ± 22.7 | 51 | 0.001 | Control group |
| 19 | Test sample in example 17 | 333.5 ± 23.5 | 39 | 0.01 | Control group |
| 20 | Test sample in example 18 | 207.9 ± 16.4 | 62 | 0.001 | Control group |
| 21 | Test sample in example 19 | 191.4 ± 20.5 | 65 | 0.001 | Control group |
| 22 | Test sample in example 20 | 180.4 ± 26.3 | 67 | 0.001 | Control group |
| 23 | Test sample in example 21 | 164.0 ± 24.2 | 70 | 0.001 | Control group |
| 24 | Test sample in example 22 | 153.1 ± 19.8 | 72 | 0.001 | Control group |
| 25 | Test sample in example 23 | 136.7 ± 20.3 | 75 | 0.001 | Control group |
|  |  |  | 54 | 0.001 | Group 12 |
|  |  |  | 43 | 0.001 | Group 17 |
|  |  |  | 49 | 0.001 | Group 18 |
|  |  |  | 59 | 0.001 | Group 19 |
|  |  |  | 34 | 0.01 | Group 20 |
|  |  |  | 28 | 0.01 | Group21 |
|  |  |  | 24 | 0.05 | Group22 |
|  |  |  | 16 | NS | Group 23 |
|  |  |  | 11 | NS | Group 24 |
| 26 | Test sample in example 24 | 159.6 ± 24.8 | 71 | 0.001 | Control group |
| 27 | Test sample in example 25 | 169.5 ± 26.3 | 69 | 0.001 | Control group |
| 28 | Test sample in example 26 | 191.4 ± 28.1 | 65 | 0.001 | Control group |
| 29 | Test sample in example 27 | 180.4 ± 26.3 | 67 | 0.001 | Control group |
| 30 | Test sample in example 28 | 169.5 ± 22.5 | 69 | 0.001 | Control group |
| 31 | Test sample in example 29 | 180.4 ± 18.9 | 67 | 0.001 | Control group |
| 32 | Test sample in example 30 | 114.8 ± 19.5 | 79 | 0.001 | Control group |
| 33 | Test sample in example 31 | 120.3 ± 16.3 | 78 | 0.001 | Control group |
| 34 | Test sample in example 32 | 125.8 ± 26.3 | 77 | 0.001 | Control group |

TABLE 3-continued

Serum total cholesterol (TC) test results

| Group No. | Diet | Mean total cholesterol (mg/dL) ± standard error | Decrease (%) | Student's t test P< | VS |
|---|---|---|---|---|---|
| 35 | Test sample in example 33 | 82.0 ± 10.5 | 85 | 0.001 | Control group |
| 36 | Test sample in example 34 | 153.1 ± 13.4 | 72 | 0.001 | Control group |
| 37 | Test sample in example 35 | 93.0 ± 15.5 | 83 | 0.001 | Control group |
| 38 | Test sample in example 36 | 114.8 ± 18.6 | 79 | 0.001 | Control group |
| 39 | Test sample in example 37 | 174.9 ± 20.4 | 68 | 0.001 | Control group |

TABLE 4

Serum triglyceride (TG) test results

| Group No. | Diet | Mean triglyceride (mg/dL) ± standard error | Decrease (%) | Student's t test P< | VS |
|---|---|---|---|---|---|
| 1 | Control (high-fat diet) | 298.5 ± 15.4 | — | — | — |
| 2 | Standard diet | 65.7 ± 9.8 | 78 | 0.001 | Control group |
| 3 | Test sample in example 1 | 244.8 ± 11.5 | 18 | NS | Control group |
| 4 | Test sample in example 2 | 268.7 ± 13.6 | 10 | NS | Control group |
| 5 | Test sample in example 3 | 253.7 ± 17.4 | 15 | NS | Control group |
| 6 | Test sample in example 4 | 274.6 ± 20.3 | 8 | NS | Control group |
| 7 | Test sample in example 5 | 292.5 ± 21.5 | 2 | NS | Control group |
| 8 | Test sample in example 6 | 289.5 ± 19.4 | 3 | NS | Control group |
| 9 | Test sample in example 7 | 292.5 ± 17.6 | 2 | NS | Control group |
| 10 | Test sample in example 8 | 286.6 ± 17.9 | 4 | NS | Control group |
| 11 | Test sample in example 9 | 289.5 ± 14.2 | 3 | NS | Control group |
| 12 | Test sample in example 10 | 209.0 ± 18.8 | 30 | 0.01 | Control group |
| 13 | Test sample in example 11 | 194.0 ± 14.1 | 35 | 0.01 | Control group |
| 14 | Test sample in example 12 | 214.9 ± 16.3 | 28 | 0.01 | Control group |
| 15 | Test sample in example 13 | 214.9 ± 23.2 | 28 | 0.01 | Control group |
| 16 | Test sample in example 14 | 232.8 ± 20.6 | 22 | 0.05 | Control group |
| 17 | Test sample in example 15 | 164.2 ± 14.3 | 45 | 0.001 | Control group |
| 18 | Test sample in example 16 | 179.1 ± 16.4 | 40 | 0.001 | Control group |
| 19 | Test sample in example 17 | 191.0 ± 17.6 | 36 | 0.01 | Control group |
| 20 | Test sample in example 18 | 131.3 ± 10.3 | 56 | 0.001 | Control group |
| 21 | Test sample in example 19 | 119.4 ± 14.7 | 60 | 0.001 | Control group |
| 22 | Test sample in example 20 | 107.5 ± 10.9 | 64 | 0.001 | Control group |
| 23 | Test sample in example 21 | 95.5 ± 11.4 | 68 | 0.001 | Control group |
| 24 | Test sample in example 22 | 74.6 ± 16.3 | 75 | 0.001 | Control group |

TABLE 4-continued

Serum triglyceride (TG) test results

| Group No. | Diet | Mean triglyceride (mg/dL) ± standard error | Decrease (%) | Student's t test P< | VS |
|---|---|---|---|---|---|
| 25 | Test sample in example 23 | 53.7 ± 12.6 | 82 | 0.001 | Control group |
|  |  |  | 74 | 0.001 | Group 12 |
|  |  |  | 67 | 0.001 | Group 17 |
|  |  |  | 70 | 0.001 | Group 18 |
|  |  |  | 72 | 0.001 | Group 19 |
|  |  |  | 59 | 0.001 | Group 20 |
|  |  |  | 55 | 0.001 | Group21 |
|  |  |  | 50 | 0.001 | Group22 |
|  |  |  | 44 | 0.001 | Group 23 |
|  |  |  | 28 | 0.01 | Group 24 |
| 26 | Test sample in example 24 | 65.6 ± 12.4 | 78 | 0.001 | Control group |
| 27 | Test sample in example 25 | 80.6 ± 16.2 | 73 | 0.001 | Control group |
| 28 | Test sample in example 26 | 89.5 ± 11.6 | 70 | 0.001 | Control group |
| 29 | Test sample in example 27 | 107.5 ± 15.3 | 64 | 0.001 | Control group |
| 30 | Test sample in example 28 | 89.5 ± 17.2 | 70 | 0.001 | Control group |
| 31 | Test sample in example 29 | 104.5 ± 9.6 | 65 | 0.001 | Control group |
| 32 | Test sample in example 30 | 38.8 ± 10.6 | 87 | 0.001 | Control group |
| 33 | Test sample in example 31 | 47.8 ± 14.2 | 84 | 0.001 | Control group |
| 34 | Test sample in example 32 | 50.7 ± 13.5 | 83 | 0.001 | Control group |
| 35 | Test sample in example 33 | 32.8 ± 16.3 | 89 | 0.001 | Control group |
| 36 | Test sample in example 34 | 74.6 ± 13.5 | 75 | 0.001 | Control group |
| 37 | Test sample in example 35 | 65.7 ± 14.2 | 78 | 0.001 | Control group |
| 38 | Test sample in example 36 | 47.8 ± 12.4 | 84 | 0.001 | Control group |
| 39 | Test sample in example 37 | 77.6 ± 12.3 | 74 | 0.001 | Control group |

TABLE 5

Serum high-density lipoprotein cholesterol (HDL-C) test results

| Group No. | Diet | Mean high-density lipoprotein cholesterol (mg/dL) ± standard error | Increase (%) | Student's t test P< | VS |
|---|---|---|---|---|---|
| 1 | Control (high-fat diet) | 35.5 ± 15.6 | — | — | — |
| 2 | Standard diet | 47.9 ± 14.3 | 35 | 0.01 | Control group |
| 3 | Test sample in example 1 | 40.8 ± 13.6 | 15 | NS | Control group |
| 4 | Test sample in example 2 | 38.3 ± 15.3 | 8 | NS | Control group |
| 5 | Test sample in example 3 | 37.6 ± 10.2 | 6 | NS | Control group |
| 6 | Test sample in example 4 | 39.1 ± 12.6 | 10 | NS | Control group |
| 7 | Test sample in example 5 | 36.9 ± 16.5 | 4 | NS | Control group |

TABLE 5-continued

Serum high-density lipoprotein cholesterol (HDL-C) test results

| Group No. | Diet | Mean high-density lipoprotein cholesterol (mg/dL) ± standard error | Increase (%) | Student's t test P< | VS |
|---|---|---|---|---|---|
| 8 | Test sample in example 6 | 36.5 ± 12.4 | 3 | NS | Control group |
| 9 | Test sample in example 7 | 36.9 ± 16.4 | 4 | NS | Control group |
| 10 | Test sample in example 8 | 36.5 ± 10.1 | 3 | NS | Control group |
| 11 | Test sample in example 9 | 36.2 ± 18.6 | 2 | NS | Control group |
| 12 | Test sample in example 10 | 44.4 ± 16.4 | 25 | 0.05 | Control group |
| 13 | Test sample in example 11 | 43.7 ± 11.8 | 23 | 0.05 | Control group |
| 14 | Test sample in example 12 | 45.4 ± 11.5 | 28 | 0.01 | Control group |
| 15 | Test sample in example 13 | 41.5 ± 16.9 | 17 | NS | Control group |
| 16 | Test sample in example 14 | 42.6 ± 10.3 | 20 | 0.05 | Control group |
| 17 | Test sample in example 15 | 47.2 ± 9.6 | 33 | 0.01 | Control group |
| 18 | Test sample in example 16 | 48.3 ± 9.7 | 36 | 0.01 | Control group |
| 19 | Test sample in example 17 | 45.4 ± 9.2 | 28 | 0.01 | Control group |
| 20 | Test sample in example 18 | 51.1 ± 10.9 | 44 | 0.001 | Control group |
| 21 | Test sample in example 19 | 53.3 ± 15.3 | 50 | 0.001 | Control group |
| 22 | Test sample in example 20 | 55.0 ± 14.7 | 55 | 0.001 | Control group |
| 23 | Test sample in example 21 | 56.4 ± 16.9 | 59 | 0.001 | Control group |
| 24 | Test sample in example 22 | 58.6 ± 14.9 | 65 | 0.001 | Control group |
| 25 | Test sample in example 23 | 60.4 ± 10.2 | 70 | 0.001 | Control group |
| | | | 36 | 0.01 | Group 12 |
| | | | 28 | 0.01 | Group 17 |
| | | | 25 | 0.05 | Group 18 |
| | | | 33 | 0.01 | Group 19 |
| | | | 18 | NS | Group 20 |
| | | | 13 | NS | Group21 |
| | | | 10 | NS | Group22 |
| | | | 7 | NS | Group 23 |
| | | | 3 | NS | Group 24 |
| 26 | Test sample in example 24 | 58.9 ± 13.5 | 66 | 0.001 | Control group |
| 27 | Test sample in example 25 | 57.5 ± 14.5 | 62 | 0.001 | Control group |
| 28 | Test sample in example 26 | 55.4 ± 16.9 | 56 | 0.001 | Control group |
| 29 | Test sample in example 27 | 54.3 ± 17.8 | 53 | 0.001 | Control group |
| 30 | Test sample in example 28 | 56.1 ± 10.5 | 58 | 0.001 | Control group |
| 31 | Test sample in example 29 | 56.4 ± 9.6 | 59 | 0.001 | Control group |
| 32 | Test sample in example 30 | 66.4 ± 9.5 | 87 | 0.001 | Control group |
| 33 | Test sample in example 31 | 66.0 ± 12.7 | 86 | 0.001 | Control group |
| 34 | Test sample in example 32 | 65.3 ± 16.4 | 84 | 0.001 | Control group |
| 35 | Test sample in example 33 | 67.5 ± 15.4 | 90 | 0.001 | Control group |
| 36 | Test sample in example 34 | 59.6 ± 9.8 | 68 | 0.001 | Control group |
| 37 | Test sample in example 35 | 67.5 ± 9.6 | 90 | 0.001 | Control group |
| 38 | Test sample in example 36 | 62.8 ± 12.3 | 77 | 0.001 | Control group |
| 39 | Test sample in example 37 | 58.9 ± 10.6 | 66 | 0.001 | Control group |

The above experimental results demonstrated that the composition of the present invention have an unexpected synergistic effect as compared single ingredient thereof.

Example 39 Preparation of Soft Capsule Formulations

Preparation of a content of a soft capsule: the nutritional composition of Example 30 was used as the content of the soft capsule.

Method for preparing a capsule shell of the soft capsule was as follows: gelatin 150 g, glycerin 90 g, purified water 180 g, caramel color 10 g, paprika red 2 g and titanium dioxide 1.5 g were weighed; the glycerin and purified water were placed into a sol tank and heated to 60° C.; the gelatin was added to the sol tank and further heated to 65° C. to be dissolved; then the caramel color, red pepper, titanium dioxide which had been dissolved and filtered were added into the sol tank, stirred for 25 min, vacuumized to exhaust bubbles to provide a solution of capsule shell; and the solution was kept at 60° C. and ready for use.

The above prepared soft capsule contents and the solution of capsule shell were subjected to pelletizing, shaping, drying, picking and packaging steps to obtain a soft capsule with a standard size of 450 mg/capsule.

Although the specific embodiments of the present invention have been described in detail, those skilled in the art will understand that various modifications and substitutions to those details may be made in light of all the teachings disclosed, all of which are within the scope of the present invention. The full scope of the invention is given by the appended claims and any equivalents thereof.

What is claimed is:

1. A composition, which comprises docosahexaenoic acid or an ester thereof, coenzyme Q10, lipoic acid, phospholipid, proanthocyanidins, soy isoflavone, lutein, *Panax* notoginsenosides and beta-glucan;
   wherein each component with the content thereof calculated according to the weight percentage is selected from the followings:
   1) 0.5% to 80% of docosahexaenoic acid or an ester thereof;
   2) 0.5% to 60% of coenzyme Q10;
   3) 0.5% to 60% of lipoic acid;
   4) 0.1% to 60% of phospholipid;
   5) 0.1% to 15% of proanthocyanidins;
   6) 0.1% to 8% of soy isoflavone;
   7) 0.1% to 10% of lutein;
   8) 0.1% to 8% of *Panax* notoginsenosides; and
   9) 0.1% to 8% of β-glucan.

2. The composition according to claim 1, comprising the followings:

a) 3 to 50 parts by weight of the docosahexaenoic acid or an ester thereof;
b) 3 to 60 parts by weight of the coenzyme Q10;
c) 3 to 50 parts by weight of the lipoic acid; and
d) 1 to 40 parts by weight of the phospholipid.

3. The composition according to claim 1, which comprises:
docosahexaenoic acid or an ester thereof, coenzyme Q10, lipoic acid and phospholipid, the parts by weight thereof being 3-43, 3-53, 3-43 and 1-33, respectively.

4. The composition according to claim 1, wherein the ester of docosahexaenoic acid is one or more selected from a group consisting of methyl docosahexaenoate, ethyl docosahexaenoate, glyceryl docosahexaenoate, isopropyl docosahexaenoate, and docosahexaenoic acid-phospholipid.

5. The composition according to claim 1, wherein the coenzyme Q10 is selected from one or two of oxidized coenzyme Q10 and reduced coenzyme Q10.

6. The composition according to claim 1, wherein the lipoic acid is selected from one or two of oxidized lipoic acids and reduced lipoic acid.

7. The composition according to claim 6, wherein the reduced lipoic acid is dihydrolipoic acid.

8. The composition according to claim 1, wherein the phospholipid is one or more selected from a group consisting of hydroxylated phospholipid, phosphatidylcholine, phosphatidylethanolamine, phosphatidylserine, phosphatidylglycerol, diphosphatidylglycerol, phosphatidylinositol, sphingomyelin.

9. The composition according to claim 1, comprising the followings:
e) 0.5 to 15 parts by weight of the proanthocyanidins;
f) 0.1 to 6 parts by weight of the soy isoflavone;
g) 0.1 to 9 parts by weight of the lutein;
h) 0.1 to 6 parts by weight of the *Panax* notoginsenosides; and
i) 0.1 to 6 parts by weight of the β-glucan.

10. The composition according to claim 1, which comprises:
proanthocyanidins, soy isoflavone, lutein, *Panax* notoginsenosides and β-glucan, the parts by weight thereof being 0.5-10, 0.1-4, 0.3-9, 0.2-4 and 0.1-4, respectively.

11. The composition according to claim 1, which further comprises a carrier oil.

12. The composition according to claim 11, wherein the carrier oil is one or more selected from a group consisting of natural vegetable fats, natural animal fats and synthetic fats.

13. The composition according to claim 12, wherein the carrier oil is one or more selected from a group consisting of saturated caprylic triglyceride and saturated capric triglyceride as well as caprylic/capric triglyceride.

14. The composition according to claim 1, which is in a dosage form of oils or suspensions.

15. The composition according to claim 1, wherein each component with the content thereof calculated according to the weight percentage is selected from the followings:
1) 5% to 60% of docosahexaenoic acid or an ester thereof;
2) 5% to 55% of coenzyme Q10;
3) 5% to 50% of lipoic acid; and
4) 2% to 35% of phospholipid.

16. The composition according to claim 1, comprising one or more selected from the followings:
a) 18 to 23 parts by weight of the docosahexaenoic acid or an ester thereof;
b) 8 to 13 parts by weight of the coenzyme Q10;
c) 38 to 43 parts by weight of the lipoic acid; and
d) 3 to 8 parts by weight of the phospholipid.

17. The composition according to claim 1, which comprises
docosahexaenoic acid or an ester thereof, coenzyme Q10, lipoic acid and phospholipid, the parts by weight thereof being 18-23, 8-13, 38-43 and 3-8, respectively.

18. The composition according to claim 1, wherein each component with content thereof calculated according to the weight percentage is selected from the followings:
(1) 0.1% to 11% of proanthocyanidins;
(2) 0.1% to 5.5% of soy isoflavone;
(3) 0.5% to 10% of lutein;
(4) 0.1% to 6% of *Panax* notoginsenosides; and
(5) 0.1% to 6% of β-glucan.

19. The composition according to claim 1, comprising one or more selected from the followings:
e) 1.8 to 2.3 parts by weight of the proanthocyanidins;
f) 0.3 to 0.5 part by weight of the soy isoflavone;
g) 1.3-1.8 parts by weight of the lutein;
h) 0.3 to 0.5 part by weight of the *Panax* notoginsenosides; and
i) 0.3 to 0.5 part by weight of the β-glucan.

20. The composition according to claim 1, which comprises:
proanthocyanidins, soy isoflavone, lutein, *Panax* notoginsenosides and β-glucan, the parts by weight thereof being 1.8-2.3, 0.3-0.5, 1.3-1.8, 0.3-0.5 and 0.3-0.5, respectively.

21. The composition according to claim 1, which is soft capsules, hard capsules, microcapsules, tablets, powders, pills, emulsions, or suspensions, by being formed together with adjuvants.

22. A method for preparing a composition according to claim 1, comprising the following steps: weighing each component and mixing to obtain the composition.

23. The method according to claim 22, wherein the step of being mixed is performed by using at least one of conventional stirring, shear emulsification and high-pressure homogenization.

24. A method for preventing and/or treating dyslipidemia or cardiovascular and cerebrovascular diseases in an individual in need thereof, comprising a step of administering to the individual a therapeutically effective amount of the composition according to claim 1.

25. The method according to claim 24, wherein the dyslipidemia includes hyperlipidemia, or one or more selected from elevated total cholesterol in the blood, elevated low-density lipoprotein cholesterol in the blood, elevated triglycerides in the blood, and reduced high-density lipoprotein cholesterol in the blood.

26. The method according to claim 24, wherein the cardiovascular and cerebrovascular disease is selected from arteriosclerosis, hypertension, hyperlipidemia, cerebral infarction, cerebral hemorrhage, coronary heart disease, angina pectoris, myocardial ischemia, myocardial infarction, heart failure and arrhythmia.

* * * * *